(12) United States Patent
Dong et al.

(10) Patent No.: US 10,202,329 B2
(45) Date of Patent: Feb. 12, 2019

(54) FERROCENE-BASED COMPOUNDS AND PALLADIUM CATALYSTS BASED THEREON FOR THE ALKOXYCARBONYLATION OF ETHYLENICALLY UNSATURATED COMPOUNDS

(71) Applicant: EVONIK DEGUSSA GMBH, Essen (DE)

(72) Inventors: Kaiwu Dong, Bo Zhou (CN); Helfried Neumann, Rostock (DE); Ralf Jackstell, Cuxhaven Altenwalde (DE); Matthias Beller, Ostseebad Nienhagen (DE); Robert Franke, Marl (DE); Dieter Hess, Marl (DE); Katrin Marie Dyballa, Recklinghausen (DE); Dirk Fridag, Haltern am See (DE); Frank Geilen, Haltern am See (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/213,453

(22) Filed: Jul. 19, 2016

(65) Prior Publication Data

US 2017/0022235 A1     Jan. 26, 2017

(30) Foreign Application Priority Data

Jul. 23, 2015 (DE) ........................ 10 2015 213 918

(51) Int. Cl.
*C07F 9/58* (2006.01)
*C07C 67/38* (2006.01)
(Continued)

(52) U.S. Cl.
CPC ........... *C07C 67/38* (2013.01); *B01J 31/2295* (2013.01); *B01J 31/24* (2013.01); *B01J 31/2404* (2013.01);
(Continued)

(58) Field of Classification Search
CPC ..................................................... C07F 9/572
See application file for complete search history.

(56) References Cited

U.S. PATENT DOCUMENTS 6,433,242 B1    8/2002  Wiese
2017/0022137 A1 1/2017  Dong et al.
(Continued)

FOREIGN PATENT DOCUMENTS

DE    10 2008 007081 A1    8/2009
EP         0 662 467 A1    7/1995
EP         1 029 839 A1    8/2000

OTHER PUBLICATIONS

U.S. Appl. No. 15/213,435, filed Jul. 19, 2016, Jennerjahn, et al.
(Continued)

*Primary Examiner* — Shawquia Jackson
(74) *Attorney, Agent, or Firm* — Smith, Gambrell & Russell, LLP

(57) ABSTRACT

The invention relates to a compound of formula (I)

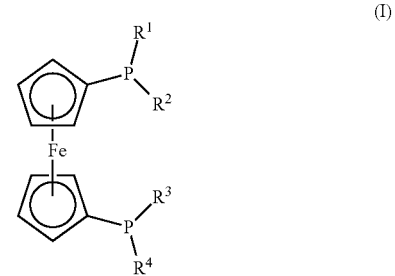

(I)

where
$R^1$ and $R^3$ are each a heteroaryl radical having five ring atoms,
$R^2$ and $R^4$ are each independently selected from —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl;
$R^1$ and $R^3$ may each independently be substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—$[(C_1$-$C_{12})$-alkyl$]_2$, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl, —COOH, —OH, —$SO_3H$, —$NH_2$, halogen;
and
$R^2$ and $R^4$, if they are —$(C_1$-$C_{12})$-alkyl, —$(C_3$-$C_{12})$-cycloalkyl, —$(C_3$-$C_{12})$-heterocycloalkyl or —$(C_6$-$C_{20})$-aryl,
may each independently be substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—$[(C_1$-$C_{12})$-alkyl$]_2$, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-
(Continued)

$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SO$_3$H, —NH$_2$, halogen;

excluding the compounds of the formulae (1) and (2)

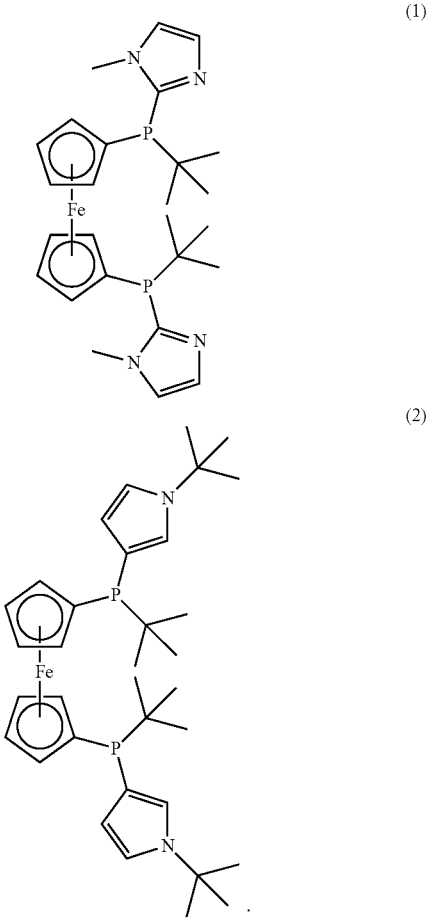

The invention further relates to precursors for preparation of the compound according to the invention, to Pd complexes comprising the compound according to the invention and to the use thereof in alkoxycarbonylation.

14 Claims, No Drawings

(51) Int. Cl.
| | |
|---|---|
| C07F 9/572 | (2006.01) |
| C07F 9/6506 | (2006.01) |
| C07F 15/00 | (2006.01) |
| B01J 31/24 | (2006.01) |
| B01J 31/22 | (2006.01) |
| C07F 9/655 | (2006.01) |
| C07F 9/6553 | (2006.01) |
| C07F 17/02 | (2006.01) |

(52) U.S. Cl.
CPC .......... *B01J 31/2409* (2013.01); *C07F 9/572* (2013.01); *C07F 9/58* (2013.01); *C07F 9/6506* (2013.01); *C07F 9/65515* (2013.01); *C07F 9/655345* (2013.01); *C07F 15/006* (2013.01); *C07F 17/02* (2013.01); *B01J 2231/321* (2013.01); *B01J 2231/49* (2013.01); *B01J 2531/0208* (2013.01); *B01J 2531/824* (2013.01); *B01J 2531/842* (2013.01)

(56) References Cited

U.S. PATENT DOCUMENTS

| | | |
|---|---|---|
| 2017/0022138 A1 | 1/2017 | Dong et al. |
| 2017/0022139 A1 | 1/2017 | Dong et al. |
| 2017/0022234 A1 | 1/2017 | Jennerjahn et al. |
| 2017/0022236 A1 | 1/2017 | Dong et al. |

OTHER PUBLICATIONS

U.S. Appl. No. 15/213,441, filed Jul. 19, 2016, Dong, et al.
U.S. Appl. No. 15/213,444, filed Jul. 19, 2016, Dong, et al.
U.S. Appl. No. 15/213,449, filed Jul. 19, 2016, Dong, et al.
U.S. Appl. No. 15/213,456, filed Jul. 19, 2016, Dong, et al.
Khokarale, S. G. et al. Zwitterion enhanced performance in palladium-phosphine catalyzed ethylene methoxycarbonylation. Catalysis Communications 44, 2014, pp. 73-75.
Clegg, William, et al. Highly active and selective catalysts for the production of methyl propanoate via the methoxycarbonylation of ethane, Chem. Commun. 1999, pp. 1877-1878.
Armarego, Wilfred L.F., et al. Purification of Laboratory Chemicals, Butterworth Heinemann (Elsevier), 6th edition, Oxford 2009. (index provided).
Harris, Robin K. et al. NMR Nomenclature, Nuclear Spin Properties and Conventions for Chemical Shifts. Pure Appl. Chem., 2001, 73, pp. 1795-1818.
Harris, Robin K. et al. Further Conventions for NMR Shielding and Chemical Shifts. Pure Appl. Chem., 2008, 80, pp. 59-84.
Search Report dated Jan. 2, 2017 for EP16180042 (8 pages).
Allouch et al, Ferrocenyl (P,N)-diphosphines incorporating pyrrolyl, imidazolyl or benzazapholyl moieties: Synthesis, coordination to group 10 metals and performances in palladium-catalyzed arylation reactions. Journal of Organometallic Chemistry, 735, 2013, pp. 38-46.
Marchenko et al. Stable N-Heterocyclic Carbenes: N-Alkyl-N' phosphanylbenzimidazol-2-ylidenes. European Journal of Organic Chemistry, 2012, pp. 4018-4033.
Database Caplus [Online] Chemical Abstracts Service, Columbus, Ohio, US; 2012, XP002765545, Found in STN Database accession No. 2012:1448458. 1 page.
Database Caplus [Online] Chemical Abstracts Service, Columbus, Ohio, US; 2000, XP002765546, Found in STN Database accession No. 2000:260134. 3 pages.
Database Caplus [Online] Chemical Abstracts Service, Columbus, Ohio, US; 1975, XP002765547, Found in STN Database accession No. 1975:4356. 1 page.
Database Caplus [Online] Chemical Abstracts Service, Columbus, Ohio, US; 1974, XP002765548, Found in STN Database accession No. 1974:48110. 1 page.
Database Caplus [Online] Chemical Abstracts Service, Columbus, Ohio, US, 1973, XP002765549, Found in STN Database accession No. 1973:546600. 1 page.
Bianchini et al. Methoxycarbonylation of Ethene by Palladium(II) Complexes with 1,1'-Bis(diphenylphosphino)ferrocene (dppf) and 1,1'-Bis(diphenylphosphino)octamethylferrocene (dppomf). Organometallics, American Chemical Society, 2003, 22, pp. 2409-2421.

FERROCENE-BASED COMPOUNDS AND PALLADIUM CATALYSTS BASED THEREON FOR THE ALKOXYCARBONYLATION OF ETHYLENICALLY UNSATURATED COMPOUNDS

The present invention relates to novel ferrocene-based compounds and to the use thereof in alkoxycarbonylation.

The alkoxycarbonylation of ethylenically unsaturated compounds is a process of increasing significance. An alkoxycarbonylation is understood to mean the reaction of ethylenically unsaturated compounds such as olefins with carbon monoxide and alcohols in the presence of a metal or metal complex and a ligand to give the corresponding esters:

Scheme 1: General reaction equation of the alkoxycarbonylation of an ethylenically unsaturated compound

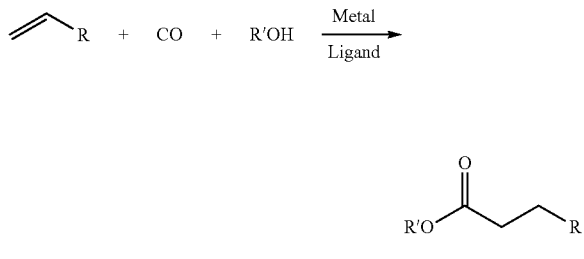

Among the alkoxycarbonylation reactions, ethene methoxycarbonylation to give 3-methylpropionate is of significance as an intermediate stage for the preparation of methyl methacrylate (S. G. Khokarale, E. J. García-Suárez, J. Xiong, U. V. Mentzel, R. Fehrmann, A. Riisager, Catalysis Communications 2014, 44, 73-75). Ethene methoxycarbonylation is conducted in methanol as solvent under mild conditions with a palladium catalyst modified by phosphine ligands.

A very good catalytic system was developed by Lucite—now Mitsubishi Rayon—and uses a ligand based on 1,2-bis(di-tert-butylphosphinomethyl)benzene (DTBPMB) (W. Clegg, G. R. Eastham, M. R. J. Elsegood, R. P. Tooze, X. L. Wang, K. Whiston, Chem. Commun. 1999, 1877-1878).

Applications of methoxycarbonylation to longer-chain substrates are described, for example, in EP 0 662 467. The patent specification describes a process for preparing dimethyl adipate from methyl 3-pentanoate. The Pd source used is Pd(II) acetate. Examples of suitable bidentate phosphine ligands that are cited include 1,1'-bis(diphenylphosphino)ferrocene, 1-(diphenylphosphino)-1'-(diisopropylphosphino)ferrocene and 1,1'-bis(isopropylphenylphosphino)ferrocene. However, the ligands achieve only unsatisfactory yields in the methoxycarbonylation of olefins, especially of long-chain olefins such as 2-octene and di-n-butene.

The technical problem on which the present invention was based is that of providing novel ferrocene-based compounds as ligands for alkoxycarbonylation reactions. These compounds are to achieve improved yields especially in the alkoxycarbonylation of ethene and long-chain olefins such as di-n-butene. More particularly, the space-time yield is to be increased in the alkoxycarbonylation reaction.

This problem is solved by diphosphine compounds of formula (I)

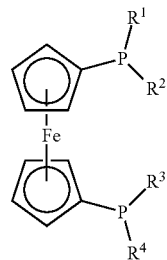

where
$R^1$ and $R^4$ are each a heteroaryl radical having five ring atoms,
$R^2$ and $R^3$ are each independently selected from —$(C_1-C_{12})$-alkyl, —$(C_3-C_{12})$-cycloalkyl, —$(C_3-C_{12})$-heterocycloalkyl, —$(C_6-C_{20})$-aryl;
$R^1$ and $R^4$ may each independently be substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —COO—$(C_1-C_{12})$-alkyl, —COO—$(C_3-C_{12})$-cycloalkyl, —CONH—$(C_1-C_{12})$-alkyl, —CONH—$(C_3-C_{12})$-cycloalkyl, —CO—$(C_1-C_{12})$-alkyl, —CO—$(C_3-C_{12})$-cycloalkyl, —N—[$(C_1-C_{12})$-alkyl]$_2$, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —$SO_3H$, —$NH_2$, halogen; and $R^2$ and $R^3$, if they are —$(C_1-C_{12})$-alkyl, —$(C_3-C_{12})$-cycloalkyl, —$(C_3-C_{12})$-heterocycloalkyl or —$(C_6-C_{20})$-aryl,
may each independently be substituted by one or more substituents selected from —$(C_1-C_{12})$-alkyl, —$(C_3-C_{12})$-cycloalkyl, —$(C_1-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_2)$-cycloalkyl, —COO—$(C_1-C_{12})$-alkyl, —COO—$(C_3-C_{12})$-cycloalkyl, —CONH—$(C_1-C_{12})$-alkyl, —CONH—$(C_3-C_{12})$-cycloalkyl, —CO—$(C_1-C_{12})$-alkyl, —CO—$(C_3-C_{12})$-cycloalkyl, —N—[$(C_1-C_{12})$-alkyl]$_2$, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —$SO_3H$, —$NH_2$, halogen;
excluding the compounds of the formulae (1) and (2)

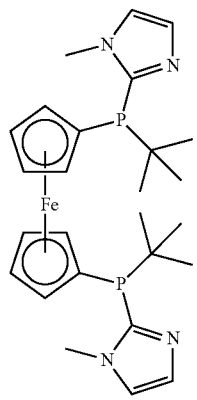

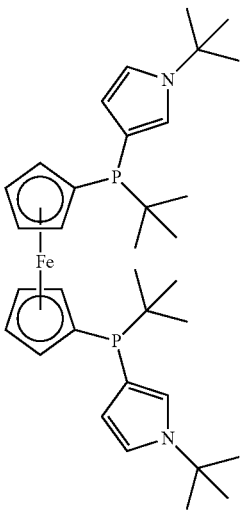

(2)

The compounds according to the invention are suitable as bidentate phosphine ligands for Pd complexes with which high yields can be achieved in the alkoxycarbonylation of a multitude of ethylenically unsaturated compounds. More particularly, the compounds according to the invention are suitable for alkoxycarbonylation of ethene and long-chain olefins such as di-n-butene.

The expression $(C_1-C_{12})$-alkyl encompasses straight-chain or branched alkyl groups having 1 to 12 carbon atoms. These are preferably $(C_1-C_8)$-alkyl groups, more preferably $(C_1-C_6)$-alkyl, most preferably $(C_1-C_4)$-alkyl.

Suitable $(C_1-C_{12})$-alkyl groups are especially methyl, ethyl, propyl, isopropyl, n-butyl, iso-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression $(C_1-C_{12})$-alkyl also apply correspondingly to the alkyl groups in —O—$(C_1-C_{12})$-alkyl, —S—$(C_1-C_{12})$-alkyl, —COO—$(C_1-C_{12})$-alkyl, —CONH—$(C_1-C_{12})$-alkyl, —CO—$(C_1-C_{12})$-alkyl and —N—$[(C_1-C_{12})$-alkyl$]_2$.

The expression $(C_3-C_{12})$-cycloalkyl encompasses mono-, bi- or tricyclic hydrocarbyl groups having 3 to 12 carbon atoms. Preferably, these groups are $(C_5-C_{12})$-cycloalkyl.

The $(C_3-C_{12})$-cycloalkyl groups have preferably 3 to 8, more preferably 5 or 6, ring atoms.

Suitable $(C_3-C_{12})$-cycloalkyl groups are especially cyclopropyl, cyclobutyl, cyclopentyl, cyclohexyl, cycloheptyl, cyclooctyl, cyclododecyl, cyclopentadecyl, norbornyl, adamantyl.

The elucidations relating to the expression $(C_3-C_{12})$-cycloalkyl also apply correspondingly to the cycloalkyl groups in —O—$(C_3-C_{12})$-cycloalkyl, —S—$(C_3-C_{12})$-cycloalkyl, —COO—$(C_3-C_{12})$-cycloalkyl, —CONH—$(C_3-C_{12})$-cycloalkyl, —CO—$(C_3-C_{12})$-cycloalkyl.

The expression $(C_3-C_{12})$-heterocycloalkyl encompasses nonaromatic, saturated or partly unsaturated cycloaliphatic groups having 3 to 12 carbon atoms, where one or more of the ring carbon atoms are replaced by heteroatoms. The $(C_3-C_{12})$-heterocycloalkyl groups have preferably 3 to 8, more preferably 5 or 6, ring atoms and are optionally substituted by aliphatic side chains. In the heterocycloalkyl groups, as opposed to the cycloalkyl groups, one or more of the ring carbon atoms are replaced by heteroatoms or heteroatom-containing groups. The heteroatoms or the heteroatom-containing groups are preferably selected from O, S, N, N(=O), C(=O), S(=O). A $(C_3-C_{12})$-heterocycloalkyl group in the context of this invention is thus also ethylene oxide.

Suitable $(C_3-C_{12})$-heterocycloalkyl groups are especially tetrahydrothiophenyl, tetrahydrofuryl, tetrahydropyranyl and dioxanyl.

The expression $(C_6-C_{20})$-aryl encompasses mono- or polycyclic aromatic hydrocarbyl radicals having 6 to 20 carbon atoms. These are preferably $(C_6-C_{14})$-aryl, more preferably $(C_6-C_{10})$-aryl.

Suitable $(C_6-C_{20})$-aryl groups are especially phenyl, naphthyl, indenyl, fluorenyl, anthracenyl, phenanthrenyl, naphthacenyl, chrysenyl, pyrenyl, coronenyl. Preferred $(C_6-C_{20})$-aryl groups are phenyl, naphthyl and anthracenyl.

The expression $(C_3-C_{20})$-heteroaryl encompasses mono- or polycyclic aromatic hydrocarbyl radicals having 3 to 20 carbon atoms, where one or more of the carbon atoms are replaced by heteroatoms. Preferred heteroatoms are N, O and S. The $(C_3-C_{20})$-heteroaryl groups have 3 to 20, preferably 6 to 14 and more preferably 6 to 10 ring atoms. Thus, for example, pyridyl in the context of this invention is a $C_6$-heteroaryl radical; furyl is a $C_5$-heteroaryl radical.

Suitable $(C_3-C_{20})$-heteroaryl groups are especially furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

The expression $(C_3-C_{20})$-heteroaryl also encompasses heteroaryl radicals having five ring atoms.

Suitable heteroaryl radicals having five ring atoms are especially furyl, thienyl, pyrolyl, imidazolyl, oxazolyl, isoxazolyl, thiazolyl, isothiazolyl, pyrazolyl, furazanyl, tetrazolyl.

The expression halogen especially encompasses fluorine, chlorine, bromine and iodine. Particular preference is given to fluorine and chlorine.

In one embodiment, the $R^1$ and $R^4$ radicals are each independently substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —$SO_3H$, —$NH_2$, halogen.

In one embodiment, the $R^1$ and $R^4$ radicals may each independently be substituted by one or more substituents selected from —$(C_1-C_{12})$-alkyl, —$(C_3-C_{12})$-cycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl.

In one embodiment, the $R^1$ and $R^4$ radicals may each independently be substituted by one or more substituents selected from —$(C_1-C_{12})$-alkyl, —$(C_3-C_{12})$-cycloalkyl, —O—$(C_1-C_{12})$-alkyl, —O—$(C_3-C_{12})$-cycloalkyl, —$(C_6-C_{20})$-aryl.

In one embodiment, the $R^1$ and $R^4$ radicals may each independently be substituted by one or more substituents selected from —$(C_1-C_{12})$-alkyl.

In one embodiment, the $R^1$ and $R^4$ radicals are unsubstituted.

In one embodiment, the $R^2$ and $R^3$ radicals, if they are —$(C_1-C_{12})$-alkyl, —$(C_3-C_{12})$-cycloalkyl, —$(C_3-C_{12})$-heterocycloalkyl or —$(C_6-C_{20})$-aryl, may each independently be substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —$SO_3H$, —$NH_2$, halogen.

In one embodiment, the $R^2$ and $R^3$ radicals, if they are —$(C_1-C_{12})$-alkyl, —$(C_3-C_{12})$-cycloalkyl, —$(C_3-C_{12})$-heterocycloalkyl or —$(C_6-C_{20})$-aryl, are each independently substituted by one or more substituents selected from —$(C_1-C_{12})$-alkyl, —$(C_3-C_{12})$-cycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl.

In one embodiment, the $R^2$ and $R^3$ radicals, if they are —$(C_1-C_{12})$-alkyl, —$(C_3-C_{12})$-cycloalkyl, —$(C_3-C_{12})$-heterocycloalkyl or —$(C_6-C_{20})$-aryl, are each independently substituted by one or more substituents selected from —$(C_1-C_{12})$-alkyl, —$(C_3-C_{12})$-cycloalkyl, —O—$(C_1-C_{12})$-alkyl, —O—$(C_3-C_{12})$-cycloalkyl, —$(C_6-C_{20})$-aryl.

In one embodiment, the $R^2$ and $R^3$ radicals, if they are —$(C_1-C_{12})$-alkyl, —$(C_3-C_{12})$-cycloalkyl, —$(C_3-C_{12})$-heterocycloalkyl or —$(C_6-C_{20})$-aryl, are each independently substituted by one or more substituents selected from —$(C_1-C_{12})$-alkyl.

In one embodiment, the $R^2$ and $R^3$ radicals are unsubstituted.

In one embodiment, $R^1$ and $R^4$ are each independently selected from furyl, thienyl, pyrrolyl, imidazolyl, oxazolyl, isoxazolyl, thiazolyl, isothiazolyl, pyrazolyl, furazanyl, tetrazolyl; preferably from furyl, thienyl, 2-pyrrolyl, 4-imidazolyl, oxazolyl, isoxazolyl, thiazolyl, isothiazolyl, pyrazolyl, furazanyl, tetrazolyl. $R^1$ and $R^4$ may be substituted as described above.

In one embodiment, $R^1$ and $R^4$ are each independently selected from 2-furyl, 3-furyl, 2-thienyl, 3-thienyl, 2-pyrrolyl, 4-imidazolyl. $R^1$ and $R^4$ may be substituted as described above.

In a particularly preferred embodiment, $R^1$ and $R^4$ are each independently selected from furyl and thienyl, especially 2-furyl and 2-thienyl. $R^1$ and $R^4$ may be substituted as described above.

In one embodiment, $R^2$ and $R^3$ are each independently selected from —$(C_1-C_{12})$-alkyl, —$(C_3-C_{12})$-cycloalkyl and —$(C_6-C_{20})$-aryl. $R^2$ and $R^3$ may be substituted as described above.

In one embodiment, $R^2$ and $R^3$ are each independently selected from —$(C_1-C_{12})$-alkyl. $R^2$ and $R^3$ may be substituted as described above.

In one embodiment, the $R^1$ and $R^4$ radicals are each a heteroaryl radical having five ring atoms selected from furyl and thienyl, and the $R^2$ and $R^3$ radicals are each —$(C_1-C_{12})$-alkyl;
where
$R^1, R^2, R^3, R^4$ may each independently be substituted by one or more of the above-described substituents.

In one embodiment, the compound has a structure of one of the formulae (16), (22) and (34):

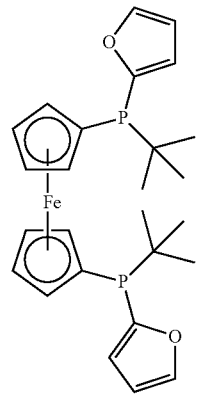

(16)

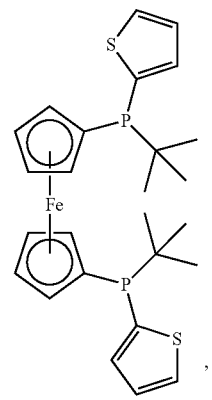

(22)

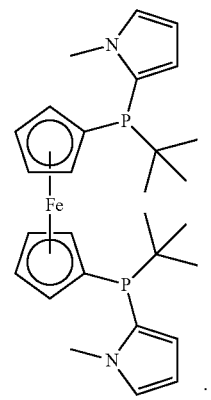

(34)

The diphosphine compounds according to the invention can be obtained, for example, by reaction of ferrocene with butyllithium and a chlorophosphine compound.

The invention thus likewise relates to novel chlorophosphine compounds which can be used as a precursor for synthesis of the diphosphine compounds according to the invention. The chlorophosphine compounds according to the invention have the formula (II)

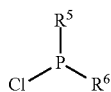

(II)

where $R^5$ is a —$(C_6-C_{20})$-heteroaryl radical having five ring atoms;

$R^6$ is selected from —$(C_1-C_{12})$-alkyl, —$(C_3-C_{12})$-cycloalkyl, —$(C_3-C_{12})$-heterocycloalkyl, —$(C_6-C_{20})$-aryl;

$R^5$ may be substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —COO—$(C_1-C_{12})$-alkyl, —COO—$(C_3-C_{12})$-cycloalkyl, —CONH—$(C_1-C_{12})$-alkyl, —CONH—$(C_3-C_{12})$-cycloalkyl, —CO—$(C_1-C_{12})$-alkyl, —CO—$(C_3-C_{12})$-cycloalkyl, —N—[$(C_1-C_{12})$-alkyl]$_2$, —$(C_6-C_{20})$-aryl, —$(C_6-C_{20})$-aryl-$(C_1-C_{12})$-alkyl, —$(C_1-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —SO$_3$H, —NH$_2$, halogen;

and $R^6$, if it is —$(C_1-C_{12})$-alkyl, —$(C_3-C_{12})$-cycloalkyl, —$(C_3-C_{12})$-heterocycloalkyl or —$(C_6-C_{20})$-aryl, may be substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —COO—$(C_1-C_{12})$-alkyl, —COO—$(C_3-C_{12})$-cycloalkyl, —CONH—$(C_1-C_{12})$-alkyl, —CONH—$(C_3-C_{12})$-cycloalkyl, —CO—$(C_1-C_{12})$-alkyl, —CO—$(C_3-C_{12})$-cycloalkyl, —N—[$(C_1-C_{12})$-alkyl]$_2$, —$(C_6-C_{20})$-aryl, —$(C_6-C_{20})$-aryl-$(C_1-C_{12})$-alkyl, —$(C_1-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —SO$_3$H, —NH$_2$, halogen;

excluding the compounds of the formulae (3) and (4)

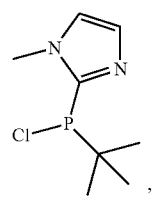

(3)

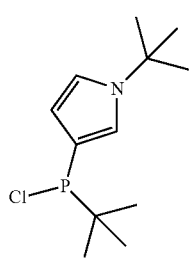

(4)

In one embodiment, $R^5$ may be substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —SO$_3$H, —NH$_2$, halogen.

In one embodiment, $R^5$ may be substituted by one or more substituents selected from —$(C_1-C_{12})$-alkyl, —$(C_3-C_{12})$-cycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl.

In one embodiment, $R^5$ may be substituted by one or more substituents selected from —$(C_1-C_{12})$-alkyl, —$(C_3-C_{12}$-cycloalkyl, —O—$(C_1-C_{12})$-alkyl.

In one embodiment, $R^5$ may be be substituted by one or more substituents selected from —$(C_1-C_{12})$-alkyl.

In one embodiment, $R^5$ is unsubstituted.

In one embodiment, $R^6$, if it is —$(C_1-C_{12})$-alkyl, —$(C_3-C_{12})$-cycloalkyl, —$(C_3-C_{12})$-heterocycloalkyl or —$(C_6-C_{20})$-aryl, may be substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —$(C_6-C_{20})$-aryl, —$(C_6-C_{20})$-aryl-$(C_3-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —SO$_3$H, —NH$_2$, halogen.

In one embodiment, $R^6$, if it is —$(C_1-C_{12})$-alkyl, —$(C_3-C_{12})$-cycloalkyl, —$(C_3-C_{12})$-heterocycloalkyl or —$(C_6-C_{20})$-aryl, may be substituted by one or more substituents selected from —$(C_1-C_{12})$-alkyl, —$(C_3-C_{12})$-cycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl.

In one embodiment, $R^6$, it is —$(C_1-C_{12})$-alkyl, —$(C_3-C_{12})$-cycloalkyl, —$(C_3-C_{12})$-heterocycloalkyl or —$(C_6-C_{20})$-aryl, may be substituted by one or more substituents selected from —$(C_1-C_{12})$-alkyl, —$(C_3-C_{12})$-cycloalkyl, —O—$(C_1-C_{12})$-alkyl, —O—$(C_3-C_{12})$-cycloalkyl, —$(C_6-C_{20})$-aryl.

In one embodiment, $R^6$, if it is —$(C_1-C_{12})$-alkyl, —$(C_3-C_{12})$-cycloalkyl, —$(C_3-C_{12})$-heterocycloalkyl or —$(C_6-C_{20})$-aryl, may be substituted by one or more substituents selected from —$(C_1-C_{12})$-alkyl.

In one embodiment, $R^6$ is unsubstituted.

In one embodiment, $R^5$ is selected from furyl, thienyl, pyrrolyl, imidazolyl, oxazolyl, isoxazolyl, thiazolyl, isothiazolyl, pyrazolyl, furazanyl, tetrazolyl; preferably from furyl, thienyl, 2-pyrrolyl, 4-imidazolyl, oxazolyl, isoxazolyl, thiazolyl, isothiazolyl, pyrazolyl, furazanyl, tetrazolyl. $R^5$ may be substituted as described above.

In one embodiment, $R^5$ is selected from 2-furyl, 3-furyl, 2-thienyl, 3-thienyl, 2-pyrrolyl, 4-imidazolyl. $R^5$ may be substituted as described above.

In a particularly preferred embodiment, $R^5$ is selected from furyl and thienyl, especially 2-furyl and 2-thienyl. $R^5$ may be substituted as described above.

In one embodiment, $R^6$ is selected from —$(C_1-C_{12})$-alkyl, —$(C_3-C_{12})$-cycloalkyl and —$(C_6-C_{20})$-aryl. $R^6$ may be substituted as described above.

In one embodiment, $R^6$ is selected from —$(C_1-C_{12})$-alkyl. $R^6$ may be substituted as described above.

In one embodiment, $R^5$ is a heteroaryl radical having five ring atoms selected from furyl and thienyl, and $R^6$ is —$(C_1-C_{12})$-alkyl;

where

R[5], R[6] may each independently be substituted by one or more of the above-described substituents.

Particularly preferred chlorophosphine compounds are chloro-2-furyl-tert-butylphosphine, chloro-2-thienyl-tert-butylphosphine and chloro-(N-methylpyrrol-2-yl)-tert-butylphosphine.

The invention further relates to complexes comprising Pd and a diphosphine compound according to the invention. In these complexes, the diphosphine compound according to the invention serves as a bidentate ligand for the metal atom. The complexes serve, for example, as catalysts for alkoxycarbonylation. With the complexes according to the invention, it is possible to achieve high yields in the alkoxycarbonylation of a multitude of different ethylenically unsaturated compounds.

The complexes according to the invention may also comprise further ligands which coordinate to the metal atom. These are, for example, ethylenically unsaturated compounds or anions. Suitable additional ligands are, for example, styrene, acetate anions, maleimides (e.g. N-methylmaleimide), 1,4-naphthoquinone, trifluoroacetate anions or chloride anions.

The invention further relates to the use of a diphosphine compound according to the invention for catalysis of an alkoxycarbonylation reaction. The compound according to the invention can especially be used as a metal complex according to the invention.

The invention also relates to a process comprising the process steps of:
a) initially charging an ethylenically unsaturated compound;
b) adding a diphosphine compound according to the invention and a compound comprising Pd,
   or adding a complex according to the invention comprising Pd and a diphosphine compound according to the invention;
c) adding an alcohol;
d) feeding in CO;
e) heating the reaction mixture, with conversion of the ethylenically unsaturated compound to an ester.

In this process, process steps a), b), c) and d) can be effected in any desired sequence. Typically, however, the addition of CO is effected after the co-reactants have been initially charged in steps a) to c). Steps d) and e) can be effected simultaneously or successively. In addition, CO can also be fed in in two or more steps, in such a way that, for example, a portion of the CO is first fed in, then the mixture is heated, and then a further portion of CO is fed in.

The ethylenically unsaturated compounds used as reactant in the process according to the invention contain one or more carbon-carbon double bonds. These compounds are also referred to hereinafter as olefins for simplification. The double bonds may be terminal or internal.

Preference is given to ethylenically unsaturated compounds having 2 to 30 carbon atoms, preferably 2 to 22 carbon atoms, more preferably 2 to 12 carbon atoms.

In one embodiment, the ethylenically unsaturated compound comprises 4 to 30 carbon atoms, preferably 6 to 22 carbon atoms, more preferably 8 to 12 carbon atoms, most preferably 8 carbon atoms.

The ethylenically unsaturated compounds may, in addition to the one or more double bonds, contain further functional groups. Preferably, the ethylenically unsaturated compound comprises one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, hydroxyl, sulphhydryl, amino, ether, thioether, aryl, heteroaryl or silyl groups and/or halogen substituents. At the same time, the ethylenically unsaturated compound preferably comprises a total of 2 to 30 carbon atoms, preferably 2 to 22 carbon atoms, more preferably 2 to 12 carbon atoms.

In one embodiment, the ethylenically unsaturated compound does not comprise any further functional groups apart from carbon-carbon double bonds.

In a particularly preferred embodiment, the ethylenically unsaturated compound is an unfunctionalized alkene having at least one double bond and 2 to 30 carbon atoms, preferably 6 to 22 carbon atoms, further preferably 8 to 12 carbon atoms, and most preferably 8 carbon atoms.

Suitable ethylenically unsaturated compounds are, for example:
ethene;
propene;
C4 olefins such as 1-butene, cis-2-butene, trans-2-butene, mixture of cis- and trans-2-butene, isobutene, 1,3-butadiene; raffinate I to III, crack-C4
C5 olefins such as 1-pentene, 2-pentene, 2-methyl-1-butene, 2-methyl-2-butene, 2-methyl-1,3-butadiene (isoprene), 1,3-pentadiene;
C6 olefins such as tetramethyleylethylene, 1,3-hexadiene, 1,3-cyclohexadiene;
C7 olefins such as 1-methylcyclohexene, 2,4-heptadiene, norbornadiene;
C8 olefins such as 1-octene, 2-octene, cyclooctene, di-n-butene, diisobutene, 1,5-cyclooctadiene, 1,7-octadiene;
C9 olefins such as tripropene;
C10 olefins such as dicyclopentadiene;
undecenes;
dodecenes;
internal C14 olefins;
internal C15 to C18 olefins;
linear or branched, cyclic, acyclic or partly cyclic, internal C15 to C30 olefins; triisobutene, tri-n-butene;
terpenes such as limonene, geraniol, farnesol, pinene, myrcene, carvone, 3-carene; polyunsaturated compounds having 18 carbon atoms, such as linoleic acid or linolenic acid; esters of unsaturated carboxylic acids, such as vinyl esters of acetic or propionic acid, alkyl esters of unsaturated carboxylic acids, methyl or ethyl esters of acrylic acid and methacrylic acid, oleic esters, methyl or ethyl oleate, esters of linoleic or linolenic acid;
vinyl compounds such as vinyl acetate, vinylcyclohexene, styrene, alpha-methylstyrene, 2-isopropenylnaphthalene;
2-methyl-2-pentenal, methyl 3-pentenoate, methacrylic anhydride.

In one variant of the process, the ethylenically unsaturated compound is selected from propene, 1-butene, cis- and/or trans-2-butene, or mixtures thereof.

In one variant of the process, the ethylenically unsaturated compound is selected from 1-pentene, cis- and/or trans-2-pentene, 2-methyl-1-butene, 2-methyl-2-butene, 3-methyl-1-butene, or mixtures thereof.

In a preferred embodiment, the ethylenically unsaturated compound is selected from ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, n-octene, 1-octene, 2-octene, or mixtures thereof In one variant, a mixture of ethylenically unsaturated compounds is used. A mixture in the context of this invention refers to a composition comprising at least two different ethylenically unsaturated compounds, where the proportion of each individual ethylenically unsaturated compound is preferably at least 5% by weight, based on the total weight of the mixture.

Preference is given to using a mixture of ethylenically unsaturated compounds each having 2 to 30 carbon atoms, preferably 4 to 22 carbon atoms, more preferably 6 to 12 carbon atoms, most preferably 8 to 10 carbon atoms.

Suitable mixtures of ethylenically unsaturated compounds are those called raffinates I to III. Raffinate I comprises 40% to 50% isobutene, 20% to 30% 1-butene, 10% to 20% cis- and trans-2-butene, up to 1% 1,3-butadiene and 10% to 20% n-butane and isobutane. Raffinate 11 is a portion of the $C_4$ fraction which arises in naphtha cracking and consists essentially of the isomeric n-butenes, isobutane and n-butane after removal of isobutene from raffinate I. Raffinate III is a portion of the $C_4$ fraction which arises in naphtha cracking and consists essentially of the isomeric n-butenes and n-butane.

A further suitable mixture is di-n-butene, also referred to as dibutene, DNB or DnB. Di-n-butene is an isomer mixture of C8 olefins which arises from the dimerization of mixtures of 1-butene, cis-2-butene and trans-2-butene. In industry, raffinate 11 or raffinate III streams are generally subjected to a catalytic oligomerization, wherein the butanes present (n/iso) emerge unchanged and the olefins present are converted fully or partly. As well as dimeric di-n-butene, higher oligomers (tributene C12, tetrabutene C16) generally also form, which have to be removed by distillation after the reaction. These can likewise be used as reactants.

In a preferred variant, a mixture comprising isobutene, 1-butene, cis- and trans-2-butene is used. Preferably, the mixture comprises 1-butene, cis- and trans-2-butene.

The alkoxycarbonylation according to the invention is catalysed by the Pd complex according to the invention. The Pd complex may either be added in process step b) as a preformed complex comprising Pd and the phosphine ligands according to the invention or be formed in situ from a compound comprising Pd and the free phosphine ligand. In this context, the compound comprising Pd is also referred to as catalyst precursor.

In the case that the catalyst is formed in situ, the ligand can be added in excess, such that the unbound ligand is also present in the reaction mixture.

In the case of the complex which is added right at the start as well, it is also possible to add further ligand, such that the unbound ligand is present in the reaction mixture.

In one variant, the compound comprising Pd is selected from palladium dichloride ($PdCl_2$), palladium(II) acetylacetonate [$Pd(acac)_2$], palladium(II) acetate [$Pd(OAc)_2$], dichloro(1,5-cyclooctadiene)palladium(II) [$Pd(cod)_2Cl_2$], bis(dibenzylideneacetone)palladium [$Pd(dba)_2$], bis(acetonitrile)dichloropalladium(II) [$Pd(CH_3CN)_2Cl_2$], palladium(cinnamyl) dichloride [$Pd(cinnamyl)Cl_2$].

Preferably, the compound comprising Pd is $PdCl_2$, $Pd(acac)_2$ or $Pd(OAc)_2$. $PdCl_2$ is particularly suitable.

The alcohol in process step c) may be branched or linear, cyclic, alicyclic, partly cyclic or aliphatic, and is especially a $C_1$- to $C_{30}$-alkanol. It is possible to use monoalcohols or polyalcohols.

The alcohol in process step c) comprises preferably 1 to 30 carbon atoms, more preferably 1 to 22 carbon atoms, especially preferably 1 to 12 carbon atoms. It may be a monoalcohol or a polyalcohol.

The alcohol may, in addition to the one or more hydroxyl groups, contain further functional groups. Preferably, the alcohol may additionally comprise one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, sulphhydryl, amino, ether, thioether, aryl, heteroaryl or silyl groups and/or halogen substituents.

In one embodiment, the alcohol does not comprise any further functional groups except for hydroxyl groups.

The alcohol may contain unsaturated and aromatic groups. However, it is preferably an aliphatic alcohol.

An aliphatic alcohol in the context of this invention refers to an alcohol which does not comprise any aromatic groups, i.e., for example, an alkanol, alkenol or alkynol.

In one embodiment, the alcohol is an alkanol having one or more hydroxyl groups and 1 to 30 carbon atoms, preferably 1 to 22 carbon atoms, more preferably 1 to 12 carbon atoms, most preferably 1 to 6 carbon atoms.

In one variant of the process, the alcohol in process step c) is selected from the group of the monoalcohols.

In one variant of the process, the alcohol in process step c) is selected from: methanol, ethanol, 1-propanol, isopropanol, isobutanol, tert-butanol, 1-butanol, 2-butanol, 1-pentanol, 2-pentanol, 3-pentanol, 1-hexanol, cyclohexanol, phenol, 2-ethylhexanol, isononanol, 2-propylheptanol.

In a preferred variant, the alcohol in process step c) is selected from methanol, ethanol, 1-propanol, 1-butanol, 1-pentanol, 1-hexanol, 2-propanol, tert-butanol, 3-pentanol, cyclohexanol, phenol, and mixtures thereof.

In one variant of the process, the alcohol in process step c) is selected from the group of the polyalcohols.

In one variant of the process, the alcohol in process step c) is selected from: diols, triols, tetraols.

In one variant of the process, the alcohol in process step c) is selected from: cyclohexane-1,2-diol, ethane-1,2-diol, propane-1,3-diol, glycerol, butane-1,2,4-triol, 2-hydroxymethylpropane-1,3-diol, 1,2,6-trihydroxyhexane, pentaerythritol, 1,1,1-tri(hydroxymethyl)ethane, catechol, resorcinol and hydroxyhydroquinone.

In one variant of the process, the alcohol in process step c) is selected from: sucrose, fructose, mannose, sorbose, galactose and glucose.

In a preferred variant of the process, the alcohol in process step c) is selected from methanol, ethanol, 1-propanol, 1-butanol, 1-pentanol, 1-hexanol.

In a particularly preferred variant of the process, the alcohol in process step c) is selected from: methanol, ethanol.

In a particularly preferred variant of the process, the alcohol in process step c) is methanol.

In one variant of the process, the alcohol in process step c) is used in excess.

In one variant of the process, the alcohol in process step c) is used simultaneously as solvent.

In one variant of the process, a further solvent is used, selected from: toluene, xylene, tetrahydrofuran (THF) and methylene chloride ($CH_2Cl_2$).

CO is fed in in step d) preferably at a partial CO pressure between 0.1 and 10 MPa (1 to 100 bar), preferably between 1 and 8 MPa (10 to 80 bar), more preferably between 2 and 4 MPa (20 to 40 bar).

The reaction mixture is heated in step e) of the process according to the invention preferably to a temperature between 10° C. and 180° C., preferably between 20 and 160° C., more preferably between 40 and 120° C., in order to convert the ethylenically unsaturated compound to an ester.

The molar ratio of the ethylenically unsaturated compound initially charged in step a) to the alcohol added in step c) is preferably between 1:1 and 1:20, more preferably 1:2 and 1:10, more preferably 1:3 and 1:4.

The mass ratio of Pd to the ethylenically unsaturated compound initially charged in step a) is preferably between 0.001% and 0.5% by weight, preferably between 0.01% and 0.1% by weight, more preferably between 0.01% and 0.05% by weight.

The molar ratio of the diphosphine compound according to the invention to Pd is preferably between 0.1:1 and 400:1, preferably between 0.5:1 and 400:1, more preferably between 1:1 and 100:1, most preferably between 2:1 and 50:1.

Preferably, the process is conducted with addition of an acid. In one variant, the process therefore additionally comprises step c'): adding an acid to the reaction mixture. This may preferably be a Brønsted or Lewis acid.

Suitable Brønsted acids preferably have a $pK_a \leq 5$, preferably an acid strength of $pK_a \leq 3$. The reported acid strength $pK_a$ is based on the $pK_a$ determined under standard conditions (25° C., 1.01325 bar). In the case of a polyprotic acid, the acid strength $pK_a$ in the context of this invention relates to the $pK_a$ of the first protolysis step.

Preferably, the acid is not a carboxylic acid.

Suitable Brønsted acids are, for example, perchloric acid, sulphuric acid, phosphoric acid, methylphosphonic acid and sulphonic acids. Preferably, the acid is sulphuric acid or a sulphonic acid. Suitable sulphonic acids are, for example, methanesulphonic acid, trifluoromethanesulphonic acid, tert-butanesulphonic acid, p-toluenesulphonic acid (PTSA), 2-hydroxypropane-2-sulphonic acid, 2,4,6-trimethylbenzenesulphonic acid and dodecylsulphonic acid. Particularly preferred acids are sulphuric acid, methanesulphonic acid, trifluoromethanesulphonic acid and p-toluenesulphonic acid.

A Lewis acid used may, for example, be aluminium triflate.

In one embodiment, the amount of acid added in step c') is 0.3 to 40 mol %, preferably 0.4 to 15 mol %, more preferably 0.5 to 5 mol %, most preferably 0.6 to 3 mol %, based on the molar amount of the ethylenically unsaturated compound used in step a).

EXAMPLES

The invention is described in detail hereinafter by working examples.

General Procedures

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Phosphorus trichloride (Aldrich) was distilled under argon before use. All preparative operations were effected in baked-out vessels. The products were characterized by means of NMR spectroscopy. Chemical shifts (δ) are reported in ppm. The $^{31}P$ NMR signals were referenced as follows: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

The recording of nuclear resonance spectra was effected on Bruker Avance 300 or Bruker Avance 400, gas chromatography analysis on Agilent GC 7890A, elemental analysis on Leco TruSpec CHNS and Varian ICP-OES 715, and ESI-TOF mass spectrometry on Thermo Electron Finnigan MAT 95-XP and Agilent 6890 N/5973 instruments.

Preparation of Precursor G tert-Butylchloro(furan-2-yl)phosphine

Scheme 2: Synthesis of precursor G

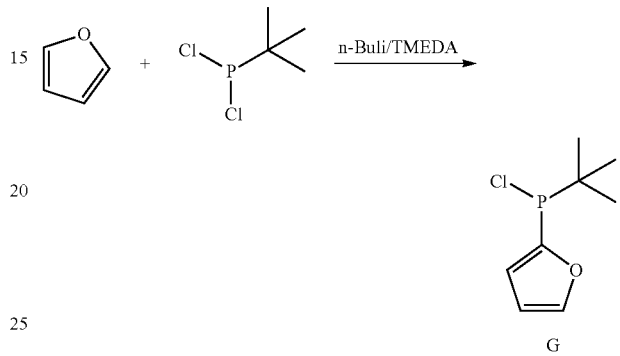

G

Chemicals used: 1.6 ml of tetramethylethylenediamine (TMEDA) (1.05 eq, 10 mmol)

6 ml of 1.6 M n-butyllithium (n-BuLi) (10 mmol, 1.05 eq)

1.5 g of dichloro(tert-butyl)phosphine (9.5 mmol)

0.7 ml of furan (9.7 mmol, 1.03 eq)

Absolute diethyl ether 0.64 g (0.7 ml, 9.4 mmol) of furan are weighed out in a 50 ml three-neck flask with thermometer and dropping funnel under argon and dissolved in 10 ml of diethyl ether. Then 1.6 ml of tetramethylethylenediamine are added to the solution. The mixture is then cooled down to −78° C. Thereafter, 6 ml of 1.6 N n-butyllithium solution in hexane are added dropwise by means of a dropping funnel. The 50 ml flask containing the reaction mixture is then left to stir at room temperature for 30 min. Subsequently, 1.5 g of tert-butyldichlorophosphine are dissolved in 20 ml of ether. The furan-n-BuLi mixture is added dropwise at −78° C. to the tert-butyldichloro-phosphine solution. Thereafter, the mixture is warmed to room temperature. Lithium chloride precipitates out. The suspension is filtered and the ether solution is distilled under reduced pressure at $10^{-1}$ Torr. The product is a colourless oil.

Yield 0.75 g, 42%

B.p.=54° C. ($10^{-1}$ Torr)

Purity (NMR)=100%, $^{31}P$ NMR ($CD_2Cl_2$, 121 MHz)=80.92 ppm, $^{13}C$ NMR ($CD_2Cl_2$, 75 MHz)=151.1 d, $J_{PC}$=56 Hz, 148.56 s, 123.65 d, $J_{PC}$=30.2 Hz, 111 d, $J_{PC}$=7.2 Hz, 35.4 d, $J_{PC}$=24.9 Hz, 25.9 d, $J_{PC}$=18.3 Hz $^1H$ NMR ($CD_2Cl_2$, 300 MHz, d1=10 s): 7.63, dd, (J=1.7 Hz, J=0.7 Hz, 1H), 6.87 td (J=2.5 Hz, J=1 Hz, 1H), 6.38 dt (J=4 Hz, J=1.7 Hz, 1H), 1.1 (d, J=14.8 Hz, 9H)

GC MS (M/Z, I (%)): 190 (19), 155 (2.5), 133 (8.9), 99 (14), 69 (23.6), 57 (100), 41 (32.4)

Preparation of Precursor H

Scheme 3: Synthesis of compounds H

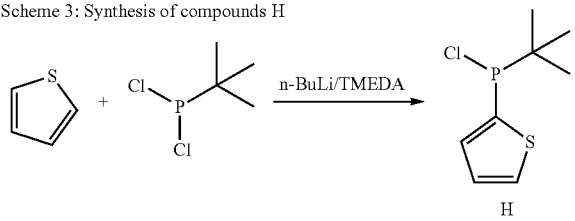

Chemicals used: 2.5 ml of TMEDA (16.6 mmol)
10 ml of 1,6 N n-butyllithium (15.7 mmol)
2.5 g of dichloro(tert-butyl)phosphine
1.2 ml of thiophene
Absolute diethyl ether 1.2 ml of thiophene are weighed out in a 50 ml three-neck flask with thermometer and dropping funnel under argon and dissolved in 10 ml of diethyl ether. Then 2.5 ml of TMEDA are added to the solution. The mixture is then cooled down to −78° C. Thereafter, 10 ml of 1.6 N n-butyllithium solution in hexane are added dropwise by means of a dropping funnel. The 50 ml flask containing the reaction mixture is subsequently left to stir at room temperature for 30 min. Subsequently, 2.5 g of tert-butyldichlorophosphine are dissolved in 20 ml of ether. Then the thiophene-n-BuLi mixture is added dropwise to the tert-butyldichlorophosphine solution at −78° C. Thereafter, the mixture is warmed to room temperature. The ether solution is distilled under reduced pressure at $10^{-1}$ Torr. The product is a colourless oil.

Yield 2.32 g, 70%
B.p.=54° C. ($10^{-1}$ Torr)
Purity (NMR)=100%,
$^{31}$P NMR (CD$_2$Cl$_2$, 121 MHz)=99.8 ppm,
$^{13}$C NMR (CD$_2$Cl$_2$, 75 MHz)=1137.7 d, ($J_{PC}$=59.9 Hz), 136.6 d ($J_{PC}$=33 Hz), 133.1 s, 127.9 d ($J_{PC}$=8.7 Hz), 35.1 d ($J_{PC}$=28.1 Hz), 25.5 d ($J_{PC}$=18.8 Hz), $^1$H NMR (CD$_2$Cl$_2$, 300 MHz, 7.59 dddd (J=0.51, J=1.1, J=4.9, J=6.0 1H), 7.34 dddd (J=1.1, J=3.5, J=7.05, J=10.6 1H), 7.03, dddd, (J=1.3, J=3.5, J=6.2 J=8.4 1H), 1.0 d (J=14.7 Hz, 9H)

Preparation of Compound 10 (Comparative Compound)

Proceeding from 1,1'-(ferrocenediyl)phenylphosphine, the strained phosphine ring is opened with PhLi and the resulting intermediate is quenched with a chlorophosphine.

Scheme 4: Synthesis of a ferrocenyl ligand

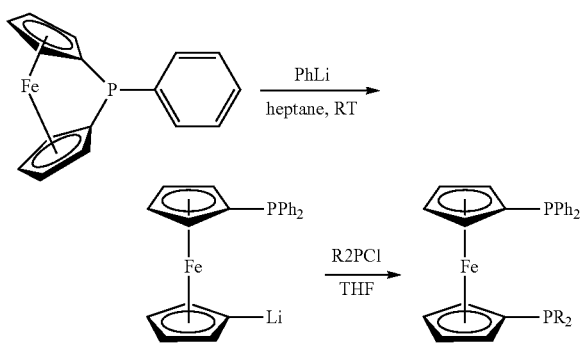

Scheme 5: Synthesis of compound 10

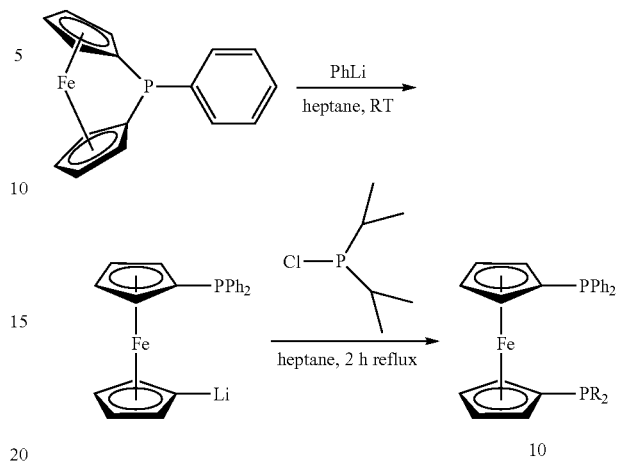

A 50 ml round-bottom flask with magnetic stirrer bar and nitrogen connection is initially charged with 1.13 mmol (565 μl) of phenyllithium (PhLi), and a solution of 1.03 mmol (300 mg) of cyclic phosphine in 20 ml of heptane is slowly added dropwise via a syringe pump. The Li salt is washed twice with heptane and admixed with 6 ml of heptane. A heptane solution of 0.8 eq (0.824 mmol, 131 μl) of ClP/Pr$_2$ in 7 ml of heptane is added dropwise to the suspension at room temperature. The red-brown suspension barely changes colour. After stirring for 20 min, the suspension is heated under reflux for 1.5 hours. The solid turns a somewhat lighter colour. Solvent is removed completely and the brown-red residue is taken up in H$_2$O and ether. The organic phase is washed twice with H$_2$O and dried over Na$_2$SO$_4$. A $^{31}$P spectrum of the ether phase is recorded. The spectrum shows 2 singlets. The chlorophosphine has been fully consumed. The ether phase is dried and 300 mg (yield: 61%) of a brown-yellow oil are obtained, which dissolves in MeOH on a water bath at 65° C. The solution is put in the freezer (−78° C.) overnight. 76 mg of a brown-yellow oil precipitate out, which is analysed by NMR spectroscopy.

$^1$H NMR (300 MHz, CDCl$_3$) δ 7.46-7.23 (m, 10H, Ph), 4.36 (m, 2H, Cp), 4.21 (m, 2H, Cp), 34.24 (m, 4H, Cp), 1.88 (m, 2H, iPr), 1.15-0.96 (m, 12H, iPr).
$^{13}$C NMR (75 MHz, CDCl$_3$) δ 139.9 (J=9.8 Hz, Ph), 133.4 (J=19.2 Hz, Ph), 128.4, 128.1, 128.0 (Ph), 77.1, 76.8, 76.2, 76.1 (Cp), 73.5 (J=14.5 Hz, Cp), 72.8 (J=2.9 Hz, Cp), 71.9 (J=10.5 Hz, Cp), 72.1 (Cp), 23.3 (J=11.0 Hz, iPr), 20.1, 20.0, 19.9, 19.8 (iPr).
$^{31}$P NMR (121 MHz, C$_6$D$_6$) δ=0.88 and −16.62

Preparation of Compound 16

1,1'-Bis((tert-butyl-2-furanyl)phosphino)ferrocene

Scheme 6: Synthesis of compound 16

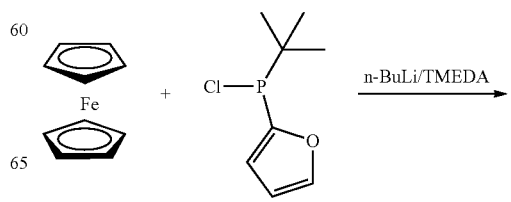

-continued

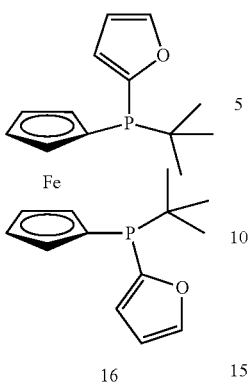

16

Chemicals used:

0.37 g of ferrocene (1.98 mmol)

2.2 ml of TMEDA (tetramethylethylenediamine) (7.34 mmol, 2.1 eq, 14.6 mmol)

10 ml of 1.6 N n-butyllithium (16 mmol, 2.28 eq)

0.75 g of chloro(tert-butyl-2-furanyl)phosphine (3.95 mmol)

Absolute diethyl ether, degassed water, methanol under argon, G 60 silica gel

In a 50 ml three-neck flask provided with a magnetic stirrer, 0.37 g of ferrocene is weighed out under argon, and 5 ml of absolute heptane are added. The ferrocene dissolves completely. Thereafter, 0.7 ml of tetramethylethylenediamine are added to the solution and then 2.9 ml of 1.6 N n-BuLi in hexane are added. The reaction solution is left to stand under cool conditions at room temperature overnight. A solid forms. The supernatant solution is removed. 10 ml of heptane are added to the solid. Then 0.75 g of tert-butylchloro(furan-2-yl)phosphine is dissolved in 5 ml of absolute THF and slowly added dropwise. This solution is stirred for one hour. Then the solvent is changed from heptane to 10 ml of diethyl ether by means of reduced pressure. Then the mixture is washed three times with 5 ml each time of water. The organic phase is dried over $Na_2SO_4$ (anhydrous). The solution is concentrated to 10 ml and column chromatography is conducted with ether. Subsequently, the solution is concentrated and crystallized from hot methanol. Orange crystals precipitate out. The liquid is decanted off and the crystals are dried.

Yield: 0.7 g $^{31}P$ NMR (acetone-$d_6$, 121 MHz)=18.3 s, s, ppm, $^{13}C$ NMR (acetone-$d_6$, 75 MHz)=147.9 s, 147.8 s, 123.4 d, $J_{PC}$=34.3 Hz, 111.0 d, $J_{PC}$=9 Hz, 78.1 d, $J_{PC}$=42.6 Hz 74.5 s, 72.99 s, 72.4 d, $J_{PC}$=9.5 Hz, 69.61 s, 31.70 d, $J_{PC}$=7.3 Hz, 28.4 d, $J_{PC}$=14.8 Hz.

$^{1}H$ NMR (acetone-$d_6$, 300 MHz): 7.85-7.8 m (2H), 6.9-6.8 m (2H), 6.45-6.4 m (2H), 4.5 m (1.3H), 4.1 m (0.9H), 3.9 m (1.3H), 3.8 m (3.7H), 2.6 m (0.7H), 0.8 (quint, J=2.3 Hz, 18H)

HRMS (ESI) m/z$^+$ calculated for $C_{26}H_{32}FeO_2P_2(M+H)^+$ 495.13; found 495.12983.

Preparation of Compound 19 (Comparative Compound)

Scheme 7: Synthesis of compound 19

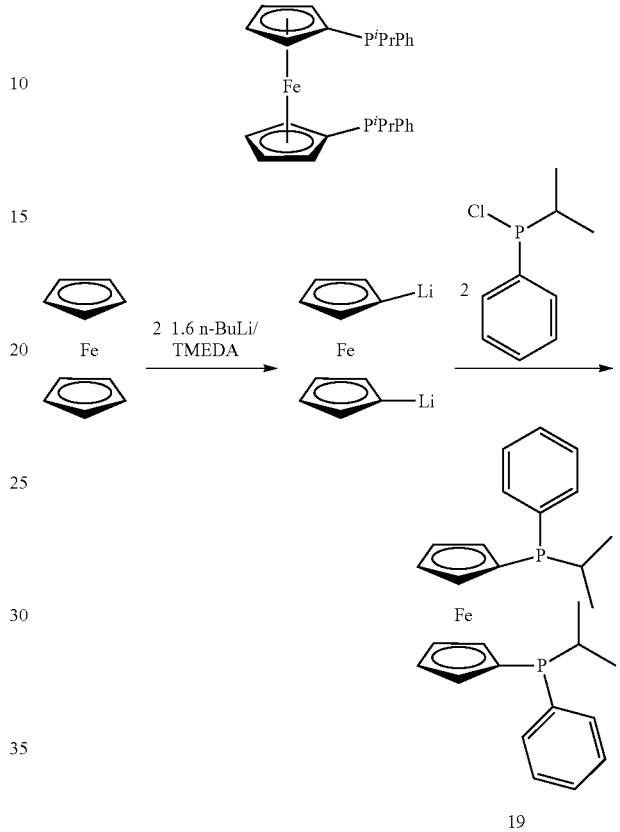

19

0.93 g of ferrocene is dissolved in 50 ml of absolute heptane in a 100 ml three-neck flask provided with a thermometer, magnetic stirrer and reflux condenser. 1.3 g of TMEDA (1.6 ml) and 7.5 ml of 1.6 M n-BuLi/hexane are added by means of syringes at room temperature. The solution is left to stand for 5 hours. Orange/brown crystals of the dilithiated ferrocene precipitate out. The supernatant solution is removed by means of a syringe. And 20 ml of absolute heptane are added. Subsequently, the chlorophosphine dissolved in 10 ml of heptane is added dropwise. The mixture is heated under reflux for one hour. After cooling, the organic phase is washed three times with 10 ml each time of degassed water. The mixture is concentrated to dryness, and 10 ml of diethyl ether are added. The solution is filtered through 10 cm of silica gel 60 under argon with diethyl ether as solvent, concentrated to dryness and crystallized from a little hot methanol to give the target product in an about 50% non-optimized yield.

Analysis:

$^{31}P$ (121 MHz, $CDCl_3$), −7.8 s, −8.15 s, $^{13}C$ (75 MHz, $CDCl_3$); 137.77, (d, J=12 Hz), 137.4 (d, J=11.3 Hz), 134.2 (d, J=20.3 Hz), 129.1 s, 128.1 (d, J=7.5 Hz), 77.4 (d, J=11.3 Hz), 75.0 (d, J=26.2 Hz), 74.0 (d, J=22.3 Hz), 72.1 bs, 71.9-71.5 m, 71.1 s, 69.0 s, 27.6 (d, J=10 Hz), 27.55 8d, J=10 Hz), 20.3-19.9 m $^{1}H$ (300 MHz, $CDCl_3$): 7.52-7.44 (m, 4H), 7.33-7.23 (m, 6H), 4.23 (sept, J=1.2 Hz, 1H), 4.1-4.0 (m, 4H), 3.93-3.9 (m, 1H), 3.87-3.84 (m, 1H), 3.58-3.54 (m, 1H), 2.1-1.9 (m, 2H), 0.99 (d, J=7 Hz, 3H), 0.94 (d, J=7 Hz, 3H), 0.83-0.7 (m, 6H)

Preparation of Compound 22

Scheme 8: Synthesis of compound 22

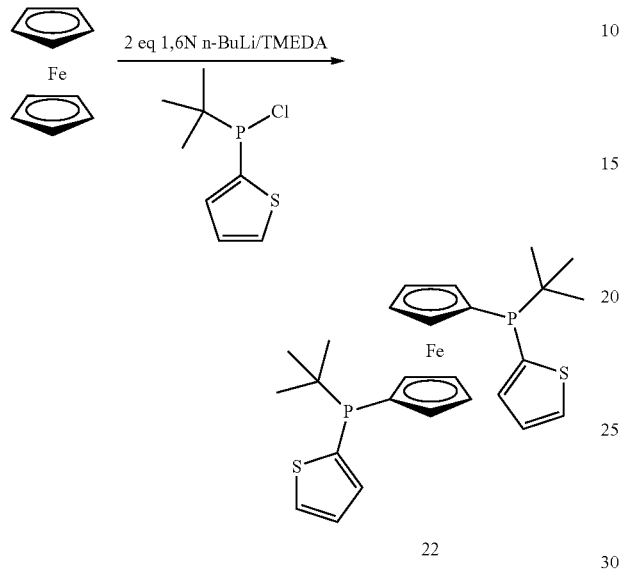

22

0.9 g of tert-butylchloro(thiophen-2-yl)phosphine (4.36 mmol) is weighed out under argon together with 5 ml of heptane in a dropping funnel. Into another 25 ml Schlenk vessel under argon is weighed 0.4 g of ferrocene (2.2 mmol), provided with a magnetic stirrer and admixed with 3 ml of absolute heptane and 0.8 ml of absolute TMEDA (tetramethylethylenediamine, 0.58 g, 5 mmol). The mixture is heated gently until the ferrocene dissolves completely. Then, at room temperature, 2.9 ml of a 1.6 N butyllithium solution (4.6 mmol) are added to the ferrocene solution. This Schlenk vessel is left to stand at 4° C. in a refrigerator for 48 hours. Large crystals of the dilithium salt of ferrocene are formed (orange-brown colour). The supernatant solution is decanted off from these under argon. And 5 ml of absolute heptane are added. While stirring, the solution containing the chlorophosphine is then added and the suspension is stirred at room temperature for one hour. The large crystals dissolve and a precipitate of lithium chloride formed is observed. Then this solution is washed three times with 5 ml each time of degassed water. The mixture is concentrated to dryness and the residue is taken up in 10 ml of absolute diethyl ether. This solution is filtered with dimethyl ether through 5 cm of G 60 silica gel. The diethyl ether is removed under reduced pressure. This leaves about 1 g of crude product. To this are added 3 ml of MeOH and the mixture is left to stand in the refrigerator at 4° C. overnight. Orange crystals are formed, which are obtained in a non-optimized yield of 500 mg as the target product (45% of theory).

Analysis:
$^{31}$P (acetone-$d_6$, 121 MHz), −6.9 s, −7.08 s
$^1$H (acetone-d6, 300 MHz) 7.76-7.7 m (2H), 7.5-7.4 m (2H), 7.2-7.1 m (2H), 4.3-4.2 m (1.4H), 4.13-4.08 m (0.7H), 3.98-3.75 m, (5H), 0.8 d ($J_{PH}$=12.8 Hz), 0.8 d ($J_{PH}$=16.1 Hz), $^{13}$C (acetone-d6, 75 MHz), 139.09 s, 138.6 d ($J_{PC}$=7 Hz), 132.4 s, 127.8 d ($J_{PC}$=10.5 Hz), 78.3 s, 77.8 s, 75.2 s, 73.6-73.3 m, 73.08 s, 72.6 d ($J_{PC}$=9.6 Hz), 72.6 d ($J_{PC}$=10 Hz), 69.7 s, 31.3 d ($J_{PC}$=9.8 Hz), 28.1 d ($J_{PC}$=15.3 Hz),
HRMS calculated for $C_{26}H_{32}Fe_1P_2S_2$: 526.07646, found: 526.07647,
MS (EI, 70 eV (Mz/%), 526 (M+, 38), 469(100), 413(94), 329(5), 299(31), 266(6)216(18)171/17)151(4.58), 115 (8)

Preparation of Compound 34

Scheme 9: Synthesis of compound 34

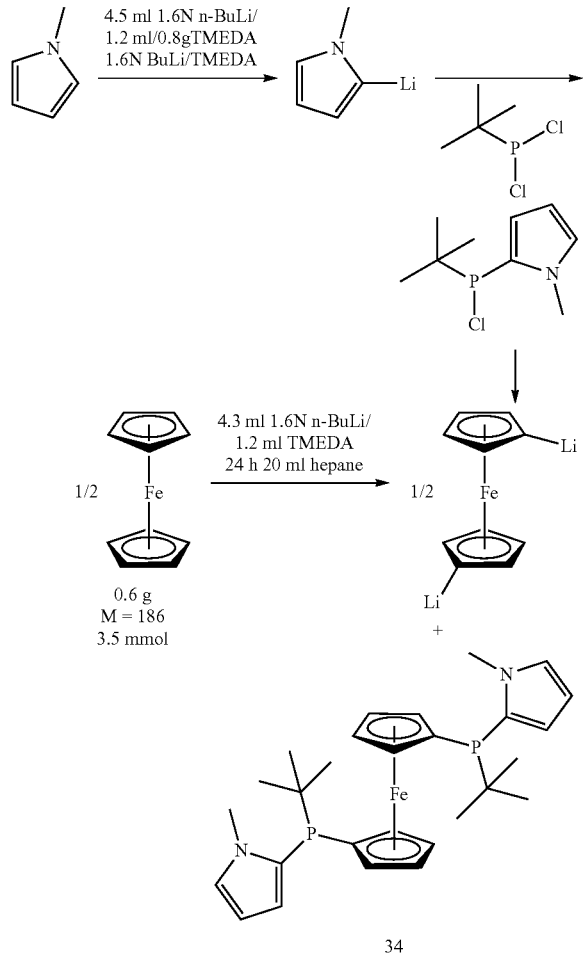

34

In a 100 ml three-neck flask provided with a magnetic stirrer and a low-temperature thermometer, under argon, 0.63 ml (0.547 g, 7.08 mmol) of N-methylpyrrole (freshly distilled from calcium hydride), 20 ml of absolute diethyl ether and 1.2 ml (0.8 g) of TMEDA are mixed while stirring. The mixture is cooled to −78° C. and, by means of a dropping funnel, 4.35 ml of 1.6 N BuLi solution in hexane (7.2 mmol) are added dropwise within 10 minutes. Then the mixture is warmed to room temperature and stirred at this temperature for half an hour. 1.12 g of tert-butyldichlorophosphine in a 100 ml Schlenk vessel are admixed with 20 ml of absolute diethyl ether under magnetic stirring, and cooled down to −78° C. At this temperature, the first solution consisting of Et$_2$O/TMEDA/lithiated N-methylpyrrole is added to the solution of the chlorophosphine while stirring.

In a further 100 ml Schlenk vessel, 0.65 g (3.5 mmol) of ferrocene is dissolved in 10 ml of heptane under argon, and 1.2 ml of TMEDA (7.1 mmol) and 4.3 ml of 1.6 N butyllithium solution are added (7.1 mmol). This solution is left to stand at 4° C. in the refrigerator overnight. Large orange crystals are formed. The supernatant solution is decanted off and 20 ml of heptane are added to the crystals. Then the solution consisting of the N-methylimidazolylchlorophosphine is added to this stirred suspension at room temperature by means of a capillary. This suspension is stirred at room temperature for one hour. Then it is washed three times with 20 ml of degassed water. Subsequently, the mixture is concentrated to dryness under reduced pressure, and the oily residue is taken up in 20 ml of absolute toluene and columned under argon with toluene as diluent through silica gel 60. Yield of 25% (450 mg).

Analytical Data

Purity (NMR)(100%)

$^{31}$P NMR (CDCl$_2$, 121 MHz)=−27.41 s, −27.52 s $^{13}$C NMR (CDCl$_2$, 75 MHz)=127.02 s, 125.34 s, 118.5 s, 108.11 s, 78.6 d, $J_{PC}$=42 Hz, 75.0 s, 72.7 d, $J_{PC}$=6.3 Hz, 71.9 s, 71.4 d, $J_{PC}$=11.5 Hz, 66.0 s, 36.2 d, $J_{PC}$=21.9 Hz, 31.0 d, $J_{PC}$=6.3 Hz, 27.75 d, $J_{PC}$=15.8 Hz, $^{1}$H NMR (CDCl$_2$, 300 MHz): 6.82-6.7 m (2H), 6.5, d,d J=1.5 Hz, J=3.7 Hz, 6.45 d,d J=1.6, J=3.7 Hz (2H), 6.18 d,d, J=2.5 Hz J=3.7 Hz, 4.2 m, 4.1-3.9 m, 3.9 s, 3.8 s, 3.8-3.74 m, 0.8 d, J=13.2 Hz

HRMS calculated for $C_{28}H_{38}FeN_2P_2$: 520.18545, found: 520.18643.

High-Pressure Experiments

Feedstocks:

Methanol (MeOH)

Ethene (also referred to as ethylene)

Di-n-butene was also referred to as follows: dibutene, DNB or DnB.

Di-n-butene is an isomer mixture of C8 olefins which arises from the dimerization of mixtures of 1-butene, cis-2-butene and trans-2-butene. In industry, raffinate II or raffinate III streams are generally subjected to a catalytic oligomerization, wherein the butanes present (n/iso) emerge unchanged and the olefins present are converted fully or partly. As well as dimeric di-n-butene, higher oligomers (tributene C12, tetrabutene C16) generally also form, which have to be removed by distillation after the reaction.

One process practised in industry for oligomerization of C4 olefins is called the "OCTOL process".

Within the patent literature, DE102008007081A1, for example, describes an oligomerization based on the OCTOL process. EP1029839A1 is concerned with the fractionation of the C8 olefins formed in the OCTOL process.

Technical di-n-butene consists generally to an extent of 5% to 30% of n-octenes, 45% to 75% of 3-methylheptenes, and to an extent of 10% to 35% of 3,4-dimethylhexenes. Preferred streams contain 10% to 20% n-octenes, 55% to 65% 3-methylheptenes, and 15% to 25% 3,4-dimethylhexenes.

para-Toluenesulphonic acid was abbreviated as follows: pTSA, PTSA or p-TSA.

PTSA in this text always refers to para-toluenesulphonic acid monohydrate.

General Method for Performance of the High-Pressure Experiments:

General Experiment Description for Reactions in Batchwise Mode:

The appropriate amounts of substrate, palladium salt, acid and alcohol are mixed under argon in a 50 ml Schlenk vessel while stirring with a magnetic stirrer.

A 100 ml steel autoclave from Parr provided with a gas inlet and a gas outlet valve, a digital pressure transducer, a temperature sensor and a ball valve, and an installed capillary for sampling, is freed of oxygen by means of vacuum and argon purging three times. Subsequently, the reaction solution from the Schlenk flask is introduced by means of a capillary into the autoclave in an argon counterflow through the ball valve. Subsequently, either the appropriate amount of CO is injected at room temperature and then the autoclave is heated up to reaction temperature (reactions that are not run under constant pressure) or the autoclave is first heated up to reaction temperature and then the CO is injected by means of a burette connected to the autoclave by means of a pressure reducer. This burette is then filled with CO to about 100 bar and, during the reaction, supplies the CO required at a constant pressure. This burette has a dead volume of about 30 ml and is provided with a digital pressure transducer. Then the reaction is conducted at the required temperature for the required time while stirring. In the course of this, by means of software (Specview from SpecView Corporation) and a Parr 4870 process controller and a 4875 power controller, data for the pressure variation in the autoclave and in the gas burette are recorded. If required, via the capillary, the GC samples are collected and analysed. For this purpose, a suitable exact amount (2-10 ml) of isooctane as internal standard is also added to the Schlenk vessel. These also give information about the course of the reaction. At the end of the reaction, the autoclave is cooled down to room temperature, the pressure is cautiously released, isooctane is added if necessary as internal standard, and a GC analysis or, in the case of new products, a GC-MS analysis is conducted as well.

General Method for Experiments in the 12-Vial Autoclaves (600 ml Parr Autoclave):

Baked-out glass vials are each initially charged with di-n-butene (DNB) and methanol, and a solution of Pd(acac)$_2$ (0.5 mg, 0.0016 mmol) and ligand (0.0064 mmol) in 0.2 ml of methanol is added, as is H$_2$SO$_4$ (solution: 1 ml of H$_2$SO$_4$ in 50 ml MeOH). In the autoclave, the mixtures are purged twice with 10 bar of CO, CO is injected to the desired pressure, and the mixtures are stirred at the desired temperature for 20 h. After the reaction has ended, isooctane (internal standard) and 1 ml of EtOAc are added in each case. The organic phase is analysed by GC.

The yields of the reactions are determined by means of GC (isooctane as internal standard).

Analysis:

GC analysis of the products from ethene: For the GC analysis, an Agilent 7890A gas chromatograph having a 30 m HP column is used. Temperature profile: 35° C., 10 min; 10° C./min to 200° C., 16.5 min; the injection volume is 1 µl with a split of 50:1. Retention time of methyl propionate: 6.158 min GC analysis of di-n-butene: For the GC analysis, an Agilent 7890A gas chromatograph having a 30 m HP5 column is used. Temperature profile: 35° C., 10 min; 10° C./min to 200° C.; the injection volume is 1 µl with a split of 50:1.

Retention times for di-n-butene and products: 10.784-13.502 min

The esters formed from di-n-butene are referred to hereinafter as MINO (methyl isononanoate).

Retention times for ether products of unknown isomer distribution: 15.312, 17.042, 17.244, 17.417 min Retention time for iso-C9 esters 19.502-20.439 min (main peak: 19.990 min)

Retention time for n-C9 esters: 20.669, 20.730, 20.884, 21.266 min.

Methanol Analysis

Methanol was pretreated in a solvent drying system: PureSolv MD Solvent Purification System, from Innovative Technology Inc. One Industrial Way, Amesbury Mass. 01013

Water Values:

Determined by Karl Fischer titration: TitraLab 580-TIM580, from Radiometer Analytical SAS (Karl Fischer titration), water content: measurement ranges, 0.1%-100% w/w, measured water content: 0.13889%

The following were used:

Technical grade methanol from Applichem: No. A2954, 5000, batch number: LOT: 3L005446 water content max. 1%

Methanol from Acros Organics (over molecular sieve): water content 0.005%, code number: 364390010, batch number: LOT 1370321

TON: turnover number, defined as moles of product per mole of catalyst metal

TOF: turnover frequency, defined as TON per unit time for the attainment of a particular conversion, e.g. 50%.

The n/iso ratio indicates the ratio of olefins converted terminally to esters to olefins converted internally to esters.

The n selectivities reported hereinafter relate to the proportion of terminal methoxycarbonylation based on the overall yield of methoxycarbonylation products.

Methoxycarbonylation of Ethene with Ligand 22

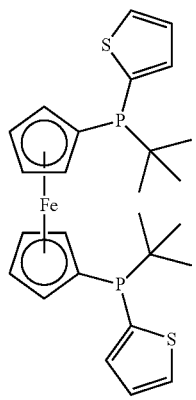

(22)

A 100 ml steel autoclave is charged with Pd(acac)$_2$ (6.52 mg, 0.04 mol %) and ligand 22 (45.5 mg, 0.16 mol %) and PTSA (61.1 mg, 0.6 mol %) and methanol (20 ml) under argon. Then 1.5 g (53.6 mmol) of ethene (3.5 from Linde AG) are transferred into the autoclave (monitoring by mass of the autoclave). After heating to a reaction temperature of 80° C. (pressure about 10 bar), CO (30 bar) is injected at this temperature. The reaction is conducted at this temperature for 20 hours. Then the autoclave is cooled down to room temperature and decompressed. The contents are transferred to a 50 ml Schlenk vessel, and isooctane (internal standard, 5.0 ml) is added. The yield and selectivity were determined by means of GC analysis (yield: 91%).

Methoxycarbonylation of Ethene with Ligand 59 (Comparative Experiment)

Scheme 10: Alkoxycarbonylation of ethene with ligand 59

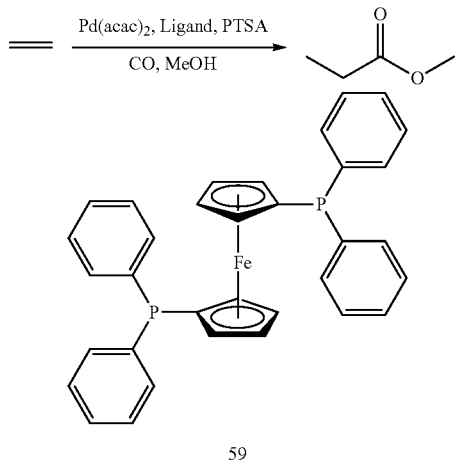

59

Ligand 59:

Ligand 59, 1,1'-bis(diphenylphosphino)ferrocene, is commercially available.

A 100 ml steel autoclave is charged with Pd(acac)$_2$ (6.52 mg, 0.04 mol %) and ligand 59 (47.9 mg, 0.16 mol %) and PTSA (61.1 mg, 0.6 mol %) and methanol (20 ml) under argon. Then 1.5 g (53.6 mmol) of ethylene (3.5 from Linde AG) are transferred into the autoclave. (Monitoring the mass of the autoclave). After the autoclave has been heated up to a reaction temperature of 80° C. (pressure about 10 bar), CO (30 bar) is injected at this temperature. At this temperature, the reaction is conducted for 20 hours. Then the autoclave is cooled down to room temperature and decompressed. The contents are transferred into a 50 ml Schlenk flask, and isooctane (internal standard, 5.0 ml) is added. The yield and selectivity were determined by means of GC analysis. (Yield: 54%).

Methoxycarbonylation of Di-n-Butene with Ligand 16

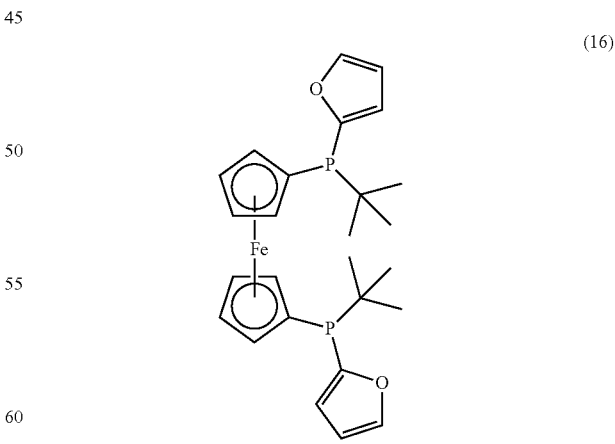

(16)

A 100 ml steel autoclave is charged under argon with Pd(acac)$_2$ (5.85 mg, 0.04 mol %), 16 (38 mg, 0.16 mol %), MeOH (20 ml), 7.54 ml of di-n-butene (48 mmol) und PTSA (54.7 mg, 0.6 mol %). Then CO is injected into the autoclave to 40 bar at room temperature. The reaction is conducted at 120° C. 20 hours. After the reaction, the autoclave is cooled down to room temperature and the pressure is released. 5 ml of isooctane are added to the solution as an internal standard. The yield and selectivity were determined by means of GC analysis (yield: 30%, n/iso: 79:21).

Methoxycarbonylation of Di-n-Butene with Ligands 10 and 19 (Comparative Experiments in a 12-Well Autoclave)

The conversion of di-n-butene with the aid of various ligands was effected by the following method:

A 50 ml Schlenk vessel was charged with [Pd(acac)$_2$] (3.9 mg, 0.04 mol %), MeSO$_3$H (methanesulphonic acid) (13 µl, 0.6 mol %) and MeOH (20 ml). A 4 ml vial was charged with ligand X (0.16 mol %), and a magnetic stirrer bar was added. Thereafter, 1.25 ml of the clear yellow solution and di-n-butene (315 µl, 2 mmol) were added with a syringe. The vial was placed into a sample holder which was in turn inserted into a 600 ml Parr autoclave under an argon atmosphere. After the autoclave had been purged three times with nitrogen, the CO pressure was adjusted to 40 bar. The reaction proceeded at 120° C. for 20 hours. On conclusion of the reaction, the autoclave was cooled down to room temperature and cautiously decompressed. Isooctane was added as internal GC standard. Yield and regioselectivity were determined by means of GC.

The results are summarized in Scheme 11 below:

Scheme 11: Catalysis results with a selection of ferrocenyl ligands

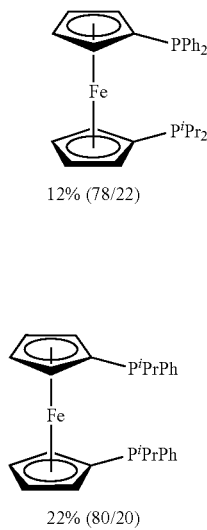

The experiments described show that the compounds according to the invention are suitable as catalyst ligands for the alkoxycarbonylation of a multitude of ethylenically unsaturated compounds, especially ethene and di-n-butene. More particularly, with the compounds according to the invention, better yields are achieved than with the bidentate phosphine ligands known from the prior art, such as 1,1'-bis(diphenylphosphino)ferrocene (ligand 59), 1-(diphenylphosphino)-1'-(diisopropylphosphino)ferrocene (ligand 10) and 1,1'-bis(isopropylphenylphosphino)ferrocene (ligand 19). In addition, the compounds according to the invention also enable the alkoxycarbonylation of long-chain olefins of industrial importance, such as di-n-butene.

The invention claimed is:

1. A compound of formula (I)

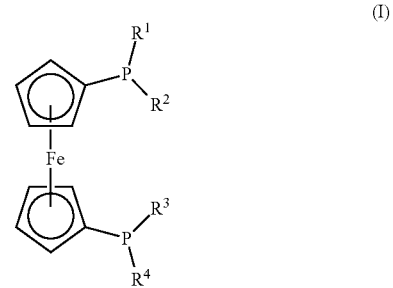

where

R$^1$ and R$^4$ are each a heteroaryl radical having five ring atoms,

R$^2$ and R$^3$ are each independently selected from —(C$_1$-C$_{12}$)-alkyl, —(C$_3$-C$_{12}$)-cycloalkyl, —(C$_3$-C$_{12}$)-heterocycloalkyl, or —(C$_6$-C$_{20}$)-aryl;

R$^1$ and R$^4$ may each independently be substituted by one or more substituents selected from —(C$_1$-C$_{12}$)-alkyl, —(C$_3$-C$_{12}$)-cycloalkyl, —(C$_3$-C$_{12}$)-heterocycloalkyl, —O—(C$_1$-C$_{12}$)-alkyl, —O—(C$_1$-C$_{12}$)-alkyl-(C$_6$-C$_{20}$)-aryl, —O—(C$_3$-C$_{12}$)-cycloalkyl, —S—(C$_1$-C$_{12}$)-alkyl, —S—(C$_3$-C$_{12}$)-cycloalkyl, —COO—(C$_1$-C$_{12}$)-alkyl, —COO—(C$_3$-C$_{12}$)-cycloalkyl, —CONH—(C$_1$-C$_{12}$)-alkyl, —CONH—(C$_3$-C$_{12}$)-cycloalkyl, —CO—(C$_1$-C$_{12}$)-alkyl, —CO—(C$_3$-C$_{12}$)-cycloalkyl, —N—[(C$_1$-C$_{12}$)-alkyl]$_2$, —(C$_6$-C$_{20}$)-aryl, —(C$_6$-C$_{20}$)-aryl-(C$_1$-C$_{12}$)-alkyl, —(C$_6$-C$_{20}$)-aryl-O—(C$_1$-C$_{12}$)-alkyl, —(C$_3$-C$_{20}$)-heteroaryl, —(C$_3$-C$_{20}$)-heteroaryl-(C$_1$-C$_{12}$)-alkyl, —(C$_3$-C$_{20}$)-heteroaryl-O—(C$_1$-C$_{12}$)-alkyl, —COOH, —OH, —SO$_3$H, —NH$_2$, or halogen;

and R$^2$ and R$^3$, if they are —(C$_1$-C$_{12}$)-alkyl, —(C$_3$-C$_{12}$)-cycloalkyl, —(C$_3$-C$_{12}$)-heterocycloalkyl or —(C$_6$-C$_{20}$)-aryl, may each independently be substituted by one or more substituents selected from —(C$_1$-C$_{12}$)-alkyl, —(C$_3$-C$_{12}$)-cycloalkyl, —(C$_3$-C$_{12}$)-heterocycloalkyl, —O—(C$_1$-C$_{12}$)-alkyl, —O—(C$_1$-C$_{12}$)-alkyl-(C$_6$-C$_{20}$)-aryl, —O—(C$_3$-C$_{12}$)-cycloalkyl, —S—(C$_1$-C$_{12}$)-alkyl, —S—(C$_3$-C$_{12}$)-cycloalkyl, —COO—(C$_1$-C$_{12}$)-alkyl, —COO—(C$_3$-C$_{12}$)-cycloalkyl, —CONH—(C$_1$-C$_{12}$)-alkyl, —CONH—(C$_3$-C$_{12}$)-cycloalkyl, —CO—(C$_1$-C$_{12}$)-alkyl, —CO—(C$_3$-C$_{12}$)-cycloalkyl, —N—[(C$_1$-C$_{12}$)-alkyl]$_2$, —(C$_6$-C$_{20}$)-aryl, —(C$_6$-C$_{20}$)-aryl-(C$_1$-C$_{12}$)-alkyl, —(C$_6$-C$_{20}$)-aryl-O—(C$_1$-C$_{12}$)-alkyl, —(C$_3$-C$_{20}$)-heteroaryl, —(C$_3$-C$_{20}$)-heteroaryl-(C$_1$-C$_{12}$)-alkyl, —(C$_3$-C$_{20}$)-heteroaryl-O—(C$_1$-C$_{12}$)-alkyl, —COOH, —OH, —SO$_3$H, —NH$_2$, or halogen;

excluding the compounds of formulae (1) and (2)

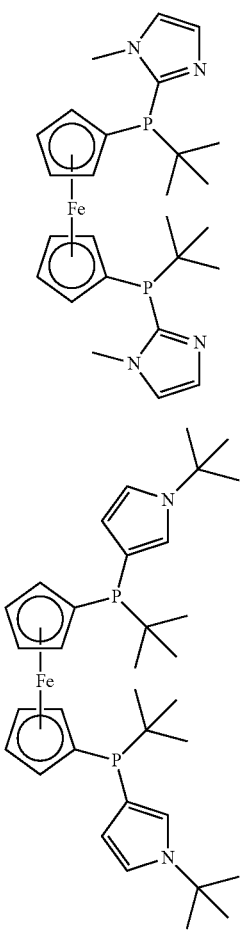

(1)

(2)

2. The compound according to claim 1,
where $R^1$ and $R^4$ are each independently selected from furyl, thienyl, 2-pyrrolyl, 4-imidazolyl, oxazolyl, isoxazolyl, thiazolyl, isothiazolyl, pyrazolyl, furazanyl, or tetrazolyl.

3. The compound according to claim 1,
where $R^1$ and $R^4$ are each independently selected from the group consisting of furyl and thienyl.

4. The compound according to claim 1,
where $R^2$ and $R^3$ are each independently selected from the group consisting of —($C_1$-$C_{12}$)-alkyl, —($C_3$-$C_{12}$)-cycloalkyl and —($C_6$-$C_{20}$)-aryl.

5. The compound according to claim 1,
where $R^2$ and $R^3$ are each —($C_1$-$C_{12}$)-alkyl.

6. The compound according to claim 1,
where $R^1$ and $R^4$ may each independently be substituted by one or more substituents selected from —($C_1$-$C_{12}$)-alkyl, —($C_3$-$C_{12}$)-cycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —($C_6$-$C_{20}$)-aryl, —($C_6$-$C_{20}$)-aryl-($C_1$-$C_{12}$)-alkyl, or —($C_6$-$C_{20}$)-aryl-O—($C_1$-$C_{12}$)-alkyl.

7. The compound according to claim 1,
where $R^2$ and $R^3$, if they are —($C_1$-$C_{12}$)-alkyl, —($C_3$-$C_{12}$)-cycloalkyl, —($C_3$-$C_{12}$)-heterocycloalkyl or —($C_6$-$C_{20}$)-aryl, may each independently be substituted by one or more substituents selected from —($C_1$-$C_{12}$)-alkyl, —($C_3$-$C_{12}$)-cycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —($C_6$-$C_{20}$)-aryl, —($C_6$-$C_{20}$)-aryl-($C_1$-$C_{12}$)-alkyl, or —($C_6$-$C_{20}$)-aryl-O—($C_1$-$C_{12}$)-alkyl.

8. The compound according to claim 1,
of one of formulae (16), (22) and (34)

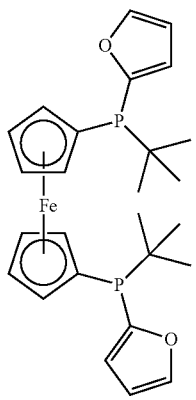

(16)

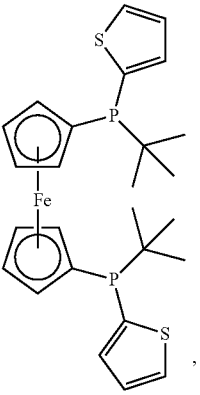

(22)

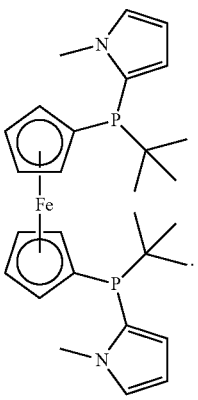

(34)

9. A complex comprising Pd and a compound according to claim 1.

10. A process for alkoxylation of long-chain olefins comprising the following process steps:

a) initially charging an ethylenically unsaturated compound;

b) adding a compound of formula (I)

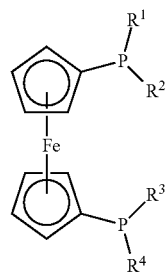

(I)

where
R¹ and R⁴ are each a heteroaryl radical having five ring atoms,
R² and R³ are each independently selected from —($C_1$-$C_{12}$)-alkyl, —($C_3$-$C_{12}$)-cycloalkyl, —($C_3$-$C_{12}$)-heterocycloalkyl, or —($C_6$-$C_{20}$)-aryl;
R¹ and R⁴ may each independently be substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SO₃H, —NH₂, or halogen;
and R² and R³, if they are —($C_1$-$C_{12}$)-alkyl, —($C_3$-$C_{12}$)-cycloalkyl, —($C_3$-$C_{12}$)-heterocycloalkyl or —($C_6$-$C_{20}$)-aryl,
may each independently be substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_rC_{12}$)-alkyl]$_2$, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SO₃H, —NH₂, or halogen;
excluding the compounds of formulae (1) and (2)

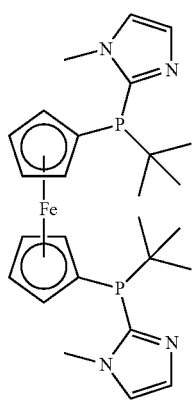

(1)

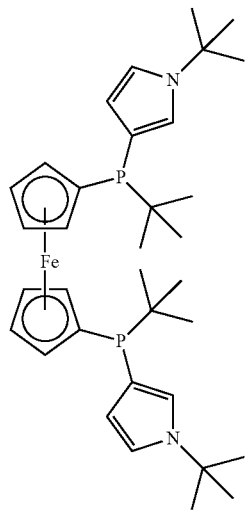

(2)

and a compound comprising Pd,
or adding a complex according to claim 9;
c) adding an alcohol;
d) feeding in CO;
e) heating the reaction mixture, with conversion of the ethylenically unsaturated compound to an ester.

11. The process according to claim 10,
wherein the ethylenically unsaturated compound is selected from the group consisting of ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, and mixtures thereof.

12. The process according to claim 10,
wherein the compound comprising Pd in process step b) is selected from palladium dichloride, palladium(II) acetylacetonate, palladium(II) acetate, dichloro(1,5-cyclooctadiene)palladium(II), bis(dibenzylideneacetone)palladium, bis(acetonitrile)dichloropalladium(II), or palladium(cinnamyl) dichloride.

13. The process according to claim 10,
wherein the alcohol in process step c) is selected from the group consisting of methanol, ethanol, 1-propanol, 1-butanol, 1-pentanol, 1-hexanol, 2-propanol, tert-butanol, 3-pentanol, cyclohexanol, phenol, and mixtures thereof.

14. A process for catalysis of an alkoxycarbonylation reaction, comprising: introducing a compound of formula (I)

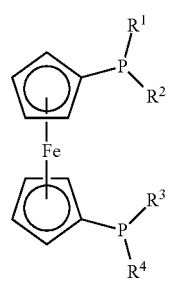

(I)

where

R¹ and R⁴ are each a heteroaryl radical having five ring atoms,

R² and R³ are each independently selected from —($C_1$-$C_{12}$)-alkyl, —($C_3$-$C_{12}$)-cycloalkyl, —($C_3$-$C_{12}$)-heterocycloalkyl, or —($C_6$-$C_{20}$)-aryl;

R¹ and R⁴ may each independently be substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SO$_3$H, —NH$_2$, or halogen;

and R² and R³, if they are —($C_1$-$C_{12}$)-alkyl, —($C_3$-$C_{12}$)-cycloalkyl, —($C_3$-$C_{12}$)-heterocycloalkyl or —($C_6$-$C_{20}$)-aryl, may each independently be substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SO$_3$H, —NH$_2$, or halogen;

excluding the compounds of formulae (1) and (2)

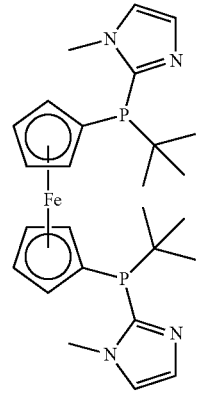

(1)

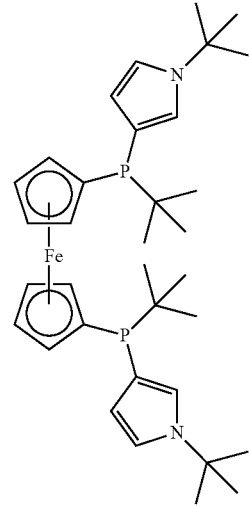

(2)

or a complex according to claim 9.

* * * * *